(12) United States Patent
Madhavi et al.

(10) Patent No.: US 7,030,102 B1
(45) Date of Patent: Apr. 18, 2006

(54) HIGHLY BIOAVAILABLE COENZYME Q-10 CYCLODEXTRIN COMPLEX

(75) Inventors: Doddabele L. Madhavi, Worcester, MA (US); Daniel I. Kagan, Belmont, MA (US)

(73) Assignee: BioActives, LLC, Belmont, MA (US)

( * ) Notice: Subject to any disclaimer, the term of this patent is extended or adjusted under 35 U.S.C. 154(b) by 47 days.

(21) Appl. No.: 10/748,096

(22) Filed: Dec. 30, 2003

Related U.S. Application Data

(60) Provisional application No. 60/468,378, filed on May 6, 2003.

(51) Int. Cl.
*A61K 31/715* (2006.01)

(52) U.S. Cl. .................. 514/58; 424/435; 424/451; 424/489

(58) Field of Classification Search .............. 514/58; 549/409; 424/435, 451, 489
See application file for complete search history.

(56) References Cited

U.S. PATENT DOCUMENTS

| | | | |
|---|---|---|---|
| 6,461,593 B1 | 10/2002 | Hanioka et al. | |
| 6,569,463 B1 * | 5/2003 | Patel et al. | 424/497 |
| 2003/0012774 A1 | 1/2003 | Moldenhauer et al. | |

FOREIGN PATENT DOCUMENTS

| | | | |
|---|---|---|---|
| JP | 59047202 A | * | 3/1984 |
| JP | 60089442 A | * | 5/1985 |

OTHER PUBLICATIONS

Gattuso et al. Synthetic Cyclic Oligosaccharides. Chem Rev. 1998, 98, pp. 1919-1958.*

"Cyclodextrins as carriers of cholesterol and fatty acids in cultivation of mycoplasmas", Appl. Envr. Microbiol., 59: 547-551, 1993).

"Comparison of impact of the different hydrophilic carriers on the properties of piperazine-containing drug", Eur. J. Pharm. Biopharm., 51: 221-225, 2001.

"Effect of inclusion complexation with cyclodextrins on photostability of nifedipine in solid state", Int. J. Pharm., 243: 107-17, 2002.

"Enhancement of dissolution and oral bioavailbilty of gliquidone with hydroxypropyl-beta-cyclodextrin", Pharmacia, 2003: 58 (11):807-10.

Physiocochemcial characterization and in vitro dissolution behavior of nicardipine hydrochloride inclusion compounds, Eur J Pharm Sci. Feb. 2002; 15(1): 79-88.

Effect of the hydrophobic nature of triacetyl-b-cyclodextrin on the complexation with nicardipine hydrochloride: physicochemical and dissolution properties of the kneaded and spray-dried complex, Chem Pharm Bull (Tokyo). Dec. 2002; 50 (12): 1597-602.

"Preparation and characterization of albendazole beta-cyclodexrin complexes", Drug Dev Ind Pharm. Dec. 1999; 25(12):12418.

"Influence of the preparation method on the physicochemical properties of ketoprofen-cyclodextrin binary systems", Int J Pharm. Mar. 1, 1999; 179(1): 117-28.

"Influence of the preparation method on the physicochemical properties of binary systems of econazole with cyclodextrins", Int J Pharm. Dec. 20, 1999; 193(1): 85-95.

"Review-Cyctodextrins in topical drug formulations: Theory and Practice", Int. J. Pharm, 225: 15-30, 2001.

* cited by examiner

*Primary Examiner*—James O. Wilson
*Assistant Examiner*—Matthew L. Fedowitz
(74) *Attorney, Agent, or Firm*—Mueller and Smith, LPA

(57) ABSTRACT

The present invention is based on the unexpected discovery that CoQ-10 can be made commercially in a highly bioavailable form suitable for topical, sublingual formulations, or for oral ingestion. One such bioavailable form is a water dispersible freeze-dried CoQ-10/γ-cyclodextrin complex. Complexation in general with γ- or α-cyclodextrin improved the cellular uptake of CoQ-10 as compared to water dispersible liposomal or micellar forms of CoQ-10. Thus, the present invention includes a highly bioavailable CoQ-10/cyclodextrin complex for use in the nutritional supplement, oral care, and pharmaceutical industry.

17 Claims, 3 Drawing Sheets

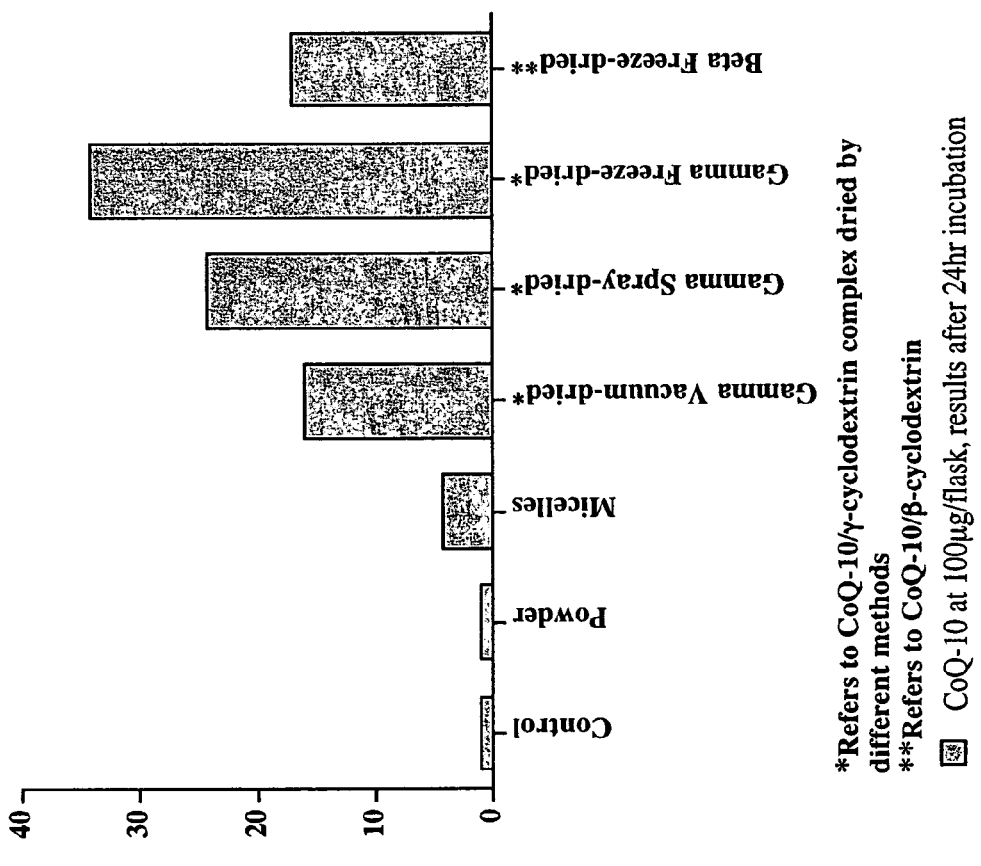
Figure 1. A Comparison of Uptake of CoQ-10 by Caco-2 Cells

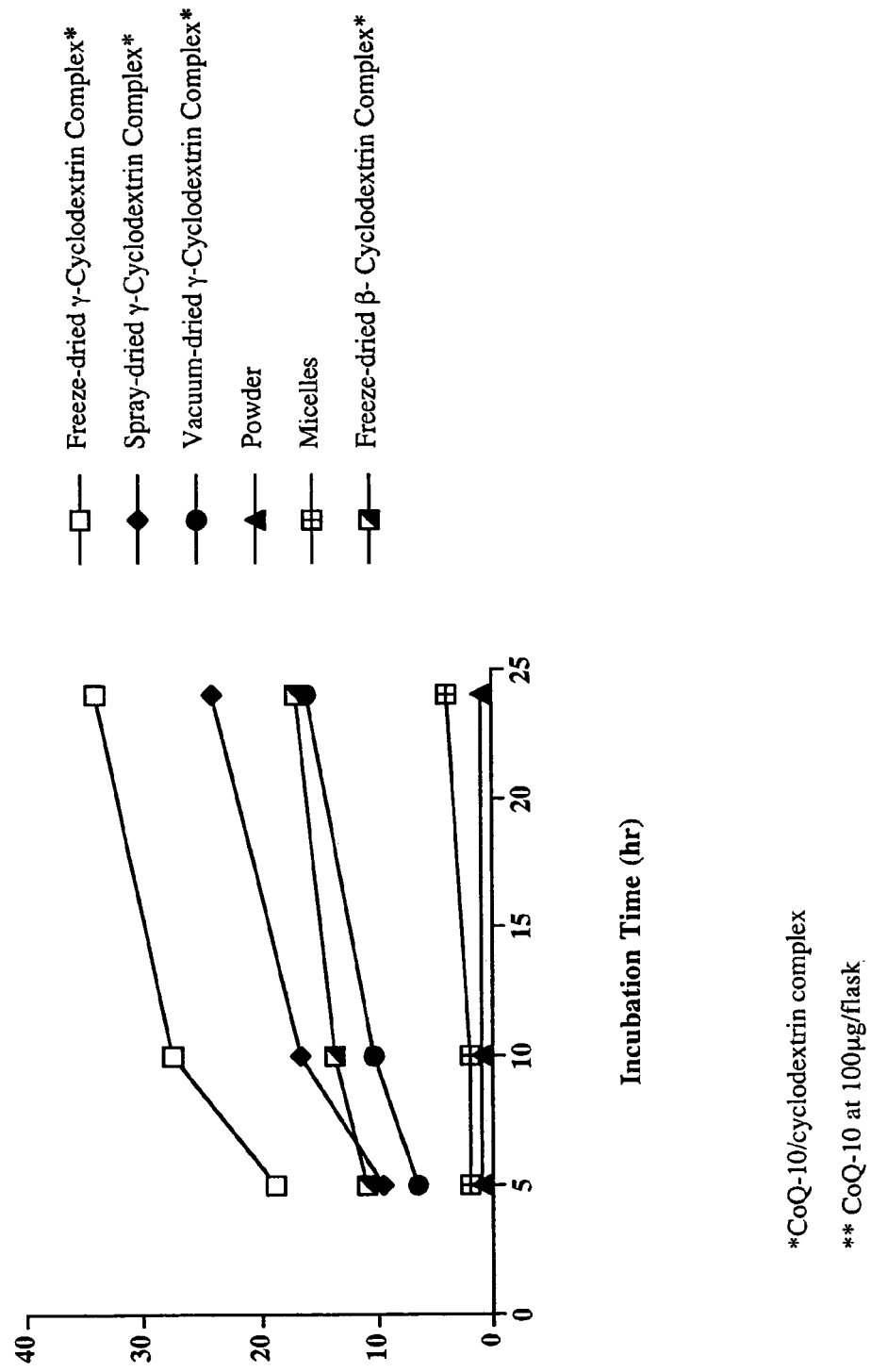
Figure 2. Effect of Incubation Time on CoQ-10 Uptake by Caco-2 Cells

Figure 3. A Comparison of Uptake of CoQ-10 by Human Gingival Fibroblasts In Vitro ▨ CoQ-10 at 100μg/flask, results after 1hr incubation.

*CoQ-10/ cyclodextrin complex dried by different methods

HIGHLY BIOAVAILABLE COENZYME Q-10 CYCLODEXTRIN COMPLEX

CROSS-REFERENCE TO RELATED APPLICATIONS

This application claims priority based on provisional application Ser. No. 60/468,378, filed on May 6, 2003, the disclosure of which is expressly incorporated herein by reference.

STATEMENT REGARDING FEDERALLY SPONSORED RESEARCH

Not applicable.

BACKGROUND OF THE INVENTION

The present invention generally relates to CoQ-10/cyclodextrin complexes and more particularly to one that is in a highly bioavailable form.

Cyclodextrins are cyclic oligosaccharides composed of 6, 7, or 8 α-(1-4)-linked anhydroglucose units. The α-, β-, and γ-cyclodextrins prepared from starch are considered natural and are GRAS according to the USFDA. Several chemically modified forms, such as, methyl, dimethyl, and hydroxypropyl-cyclodextrins have been developed.

Coenzyme Q-10 (ubiquinone or CoQ-10) is a strongly lipophilic molecule, insoluble in aqueous solution and having poor bioavailability in humans. CoQ-10 has therapeutic effects in several disease conditions, such as, for example, cardiovascular disease, periodontal diseases (U.S. Pat. No. 6,461,593), high blood pressure, and Parkinson's disease. Hence, several attempts have been made to improve its bioavailability using emulsifying agents, surfactants, and oil-based vehicles which solubilize CoQ-10. Since CoQ-10 is a lipophilic molecule, micellarizarion and transfer to the aqueous phase is necessary for intestinal absorption. Formulations containing a fully solubilized form of CoQ-10 facilitate incorporation of CoQ-10 into the micellar phase. One of the disadvantages of such formulations is the limited solubility of CoQ-10 in oil or surfactant mixtures. Incorporation of therapeutic concentrations of CoQ-10 in the nutritional supplements may not be feasible for the manufacturer or economical for the consumer.

It is known in the art that there is a deficiency of CoQ-10 in diseased gingival tissue and that correction of the deficiency improves the mechanisms of immune system in the cells. CoQ-10 dissolved in vegetable oil or in a mixture of surfactants has been proposed for oral care applications. The soluble CoQ-10 has been incorporated into, inter alia, tooth pastes, mouthwashes, or lozenges. Such solubilized forms of CoQ-10 present several problems in oral care formulations. The oily nature of the CoQ-10 solubilized in vegetable oils limits its usage in oral care products, such as mouthwash or toothpaste. The formulation may become unstable with phase separation or the oily aftertaste may create adverse consumer reaction. CoQ-10 dissolved in surfactant mixtures again has limitations in terms of usage. Higher levels of surfactant mixtures can destabilize the oral care formulations. Hence, incorporation of therapeutic levels of CoQ-10 using such solubilized forms may not be commercially feasible.

Complexation of CoQ-10 with cyclodextrins has been tried by a few investigators to improve the dissolution properties and stability of the compound. However, most of the studies use chemically modified cyclodextrins, especially methyl and dimethyl β-cyclodextrins. For example, Japanese Patent JP59047202 describes complexation with methyl β-cyclodextrin with improved solubility for oral or parenteral administration. The publication by Ueno et al. (1989) describes improvement in the dissolution and absorption of CoQ-10 by complexation with dimethyl β-cyclodextrin.

However, these publications do not indicate as to whether complexation with natural cyclodextrins, such as γ- or β-cyclodextrin, will improve the cellular uptake of CoQ-10. It is well known in the art that complexation with different cyclodextrins results in products with varying properties. For example, dimethyl β-cyclodextrin was reported to dramatically enhance the absorption of insulin, while hydroxypropyl β-cyclodextrin had no significant effect (Shao et al., 1994). Based on the solubility profile of the natural cyclodextrins, complexes with β-cyclodextrin are generally less soluble as compared to the γ-cyclodextrin complexes.

Some of the drawbacks of using chemically modified cyclodextrins include, inter alia, unexpected changes in the solubility behavior, safety issues, and commercial availability. For example, dimethyl β-cyclodextrin precipitates out of solution as the temperature is raised to 55° C. It also is reported to exert a detergent-like effect on the biological membranes. In a study determining the intestinal safety of water-soluble α-cyclodextrin derivatives using a Caco2 intestinal cell model, dimethyl β-cyclodextrin showed a dose dependent cytotoxicity (Totterman et al., 1997). In the same model, maltosyl-α-cyclodextrin was less toxic as compared to α-cyclodextrin, while maltosyl β-cyclodextrin and β-cyclodextrin showed similar effects. γ-Cyclodextrin showed the least effect even at a relatively high concentration of 150 mM (Ono et al., 2001).

Complexation of natural cyclodextrins with CoQ10 has been reported in the art. In a series of publications Lutka and Pawlaczyk (1995; 1996a,b; 1997) have described preparing the complexes using a kneading method or a heating method. Both the methods have several disadvantages for scale-up and commercial production.

Japanese patent No. JP56109590 describes complexation with β- and γ-cyclodextrins and drying the complex under reduced pressure. U.S. Patent Application Publication No. 2003/0012774 A1 describes a method of producing the γ-cyclodextrin complex by homogenization/micronization and energy input. The complex is dried in the oven at 55° C. The published application, however, does not explore the effects of drying the complex to determine a suitable commercial method for large-scale production. It is well known that drying methods, such as spray drying, freeze drying, or vacuum drying, can affect the final yield, stability of the active component, and dissolution properties of the product. Also, none of these publications have any information on the effects of complexation on the absorption of CoQ-10 from the cyclodextrin complexes either in vitro or in vivo. JP60089442 reports an aqueous complex of CoQ-10 and γ-cyclodextrin that is said to have sustained release after gastric administration. Cyclodextrin/CoQ-10 complexes for skin preparations are reported in EP 1174109 (2002). Skin care products containing combinations of biotin, ubiquinone, and cyclodextrins (including γ-cyclodextrin) are reported in DE10139851 (WO203026603).

BRIEF SUMMARY OF THE INVENTION

The present invention is based on the unexpected discovery that CoQ-10 can be made commercially in a highly bioavailable form suitable for topical, sublingual formulations, or for oral ingestion. One such preferred bioavailable form is a water dispersible freeze-dried CoQ-10/γ-cyclodextrin complex. It is obvious to those skilled in the art that the complex also can be dried by spray-drying or vacuum-drying with improved bioavailability over CoQ-10 powder. The inventive process provides a commercial product, which can be used to increase the concentration of CoQ-10 in formulations to therapeutic levels without any adverse effects on formulation or sensory properties of the final product. Complexation in general with γ- or β-cyclodextrin improved the cellular uptake of CoQ-10, as compared to water dispersible liposomal or micellar forms of CoQ-10. Thus, the present invention includes a highly bioavailable CoQ-10/cyclodextrin complex for use in the nutritional supplement, oral care, and pharmaceutical industries.

An in vitro bioavailability study using Caco2 intestinal cells (indicative of in vivo absorption) showed a highly significant uptake from the cyclodextrin complexes as compared to a micellar or liposomal form of CoQ-10. The study indicated that even in the absence of micellarization, CoQ-10 could be absorbed from an aqueous dispersion of the complex. In another in vitro study using HGF-1 human gingival cells, the cyclodextrin complexes showed significant uptake as compared to the liposomal CoQ-10. Unexpectedly, the freeze-dried γ-cyclodextrin complex showed the highest uptake in both cell lines as compared to other drying methods.

Another embodiment of the present invention is a method for making a bioavailable coenzyme Q-10 complex for animal ingestion. This method includes preparing a coenzyme Q-10/cyclodextrin complex and administering said complex to an animal. The preferred animal is a human with the route of administration being oral ingestion. The form of the complex for ingestion can be a hard gelatin capsule, tablet, or wafer, which may contain other ingredients, both active and inactive. The complex also can be further formulated with excipients suitable for soft gelatin capsules, such as, for example, vegetable oils, waxes, lecithin, and surfactants such as, for example, tween-80.

A further embodiment of the present invention is a method for making a water dispersible bioavailable coenzyme Q-10 complex for human oral care products. This method includes preparing the coenzyme Q-10/cyclodextrin complex, formulating the complex in oral care products, such as, for example, mouthwash, chewing gum, spray, toothpaste, lozenges, or a sublingual formulation, which may contain other ingredients, both active and inactive.

BRIEF DESCRIPTION OF THE DRAWINGS

For a fuller understanding of the nature and advantages of the present invention, reference should be had to the following detailed description taken in connection with the accompanying drawings, in which:

FIG. 1 represents a comparison of uptake of CoQ-10 by Caco2 cells after 24-hours exposure, as reported in Example 1;

FIG. 2 represents the uptake of CoQ-10 by Caco2 cells over a period of incubation; and FIG. 3 represents a comparison of uptake of CoQ-10 by human gingival fibroblast cells after 1 hr exposure, as reported in Example 2.

These drawings will be described below in greater detail in Examples 1 and 2, below.

DETAILED DESCRIPTION OF THE INVENTION

One aspect of the present invention is a highly bioavailable form of CoQ-10 complexed with β- and γ-cyclodextrin for use in the nutritional supplement, oral care, and pharmaceutical industries. Commercially available crystalline CoQ-10, α-, β- γ-, and hydroxypropylβ-cyclodextrins were used for complexation. The molar ratio of cyclodextrin to CoQ-10 can range, for example, from about 0.5:1 to 10:1, and from about 1:1 or 2:1 for commercial production. The CoQ-10 concentration in the complex can range, for example, from about 0.1 to 30% (w/w). The CoQ-10/cyclodextrin complex (1:2 molar) was prepared based on methods known in the art in aqueous slurry at room temperature using homogenization for 2–4 hours. The mixture was kept under refrigeration overnight before drying. Based on dispersion properties and stability of the inclusion complexes formed, the β- and γ-cyclodextrin complexes were selected for further processing and in vitro studies.

The aqueous slurry was dried by freeze-drying using a semi-commercial tray freeze dryer (Virtis). The slurry also was dried under vacuum at 50° C. (simulating published methods) and by spray-drying. The dried product can be micronized or ground and/sieved to form a uniform powder suitable for further applications or formulations. Of the three drying methods tested, freeze-drying resulted in the finest particle size of <75 microns, as expected. It is obvious to those skilled in the art that micronization of the complex further improves the dissolution and uptake of the complex. The product obtained by any of the drying methods is a light yellow powder containing 20–24% CoQ-10, suitable for capsules, tablets, and further formulations. Unexpectedly, the commercial methods of drying the complex had an effect on the properties of the product. Based on the results of cellular uptake studies of the γ-cyclodextrin complex, the β-cyclodextrin complex was prepared by freeze-drying.

The cellular uptake of the CoQ-10 from the cyclodextrin complexes was determined in vitro in model cell culture systems. For example, the uptake was determined using an in vitro Caco2 intestinal cell culture model indicative of in vivo intestinal absorption. This cell line has been used as a model system to examine the selective characteristics of intestinal absorption of compounds, such as vitamin E (Traber et al., 1990), retinol, beta lactoglobulin, palmitic acid (Puyol et al., 1995), carotenoids (Garrett et al., 1999), and polyamines (Turchanowa et al., 2001). The cells spontaneously differentiate at confluency into cells that exhibit phenotypic properties that are similar to those of mature enterocytes, including a highly differentiated brush border. CoQ-10 incorporated into mixed micelles was used for comparison.

The results of testing the present invention showed a highly significant uptake from the cyclodextrin complexes, as compared to a micellar form of CoQ-10. Of the three drying methods tested, the highest uptake was observed unexpectedly with the freeze-dried γ-cyclodextrin complex. The study indicated that even in the absence of micellarization, CoQ-10 could be absorbed from an aqueous dispersion of the complex irrespective of the drying method. Complexation with β-cyclodextrin also significantly improved the uptake of CoQ-10.

Another example of an in vitro model system is the human gingival fibroblast culture. The in vitro uptake studies with the cyclodextrin complexes (β- and γ-complexes) indicated a significant improvement in the uptake of CoQ-10 by the gingival cells, as compared to a water dispersible liposomal form of CoQ-10 powder. Again, the highest uptake was observed with the freeze-dried γ-cyclodextrin complex.

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the precepts thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference.

EXAMPLES

Example 1

In Vitro Uptake of CoQ-10 in Caco2 Cells

The uptake of CoQ-10 from the cyclodextrin complex dried by different methods was compared to commercially available CoQ-10 powder (99% pure, used in hard capsules) and CoQ-10 powder incorporated into mixed micelles, simulating the digestive process.

Sample Preparation

The mixed micelles were prepared by the method of Garrett et al. (1999) using sodium taurocholate (bile salt), mono-acylglycerol, oleic acid, phosphatidyl choline, lysophosphatidylcholine, and CoQ-10 in phosphate buffered saline (PBS). The CoQ-10/cyclodextrin complexes were dispersed in PBS. The stock solutions contained 30 mg CoQ-10/10 ml.

Cellular Uptake

The cellular uptake of CoQ-10 as a function of media concentration and exposure time was determined based on the method of Garrett et al. (1999). Caco-2 (ATCC, Rockville, Md.) cells were maintained in high glucose DMEM with 15 mM HEPES and 10% heat inactivated fetal bovine serum, nonessential amino acids, glutamine, and pyruvate in a humidified atmosphere at 5% $CO_2$ and 37° C. The cells were allowed to reach confluency (5–6 days after subculture) and differentiate (14 days) in 25 $cm^2$ flasks before the start of the experiment.

The stock test samples were diluted in the culture medium for the experiment. The monolayers were washed with PBS before adding the test samples at known CoQ-10 concentration (100 μg/flask). The control flasks had an equivalent amount of PBS in the medium. The cultures were incubated as before and the CoQ-10 uptake was terminated at indicated times. The medium was removed and the monolayers were washed with PBS, followed by three washes with 5 mM sodium taurocholate in PBS. The bile salt wash removes the CoQ-10 adhering to cell surfaces. The cells were scraped into cold PBS and pelleted using centrifugation. The pellets were immediately suspended in 3 ml hexane:ethanol (50:20) and stored frozen at −20° C. till analysis. The results are the average of duplicate experiments. The pelleted cells were extracted twice with hexane:ethanol (50:20) after a freeze-thaw cycle, followed by two extractions with diethyl ether. The extracts were combined, evaporated to dryness with $N_2$ gas. The residue was dissolved in 0.2 ml of acetonitrile: tetrahydrofuran (55:40) and CoQ-10 content was estimated by reverse phase HPLC. Standard CoQ-10 (Sigma) was used for calibration. A Hitachi HPLC system equipped with a diode array detector and Waters Nova-Pak C-18 column, 4μ, 150×3.9 mm was used for the studies. The mobile phase was acetonitrile:tetrahydrofuran (55:40):water (93:7) at a flow rate of 1 ml/min. The chromatograms were monitored at 275 nm.

The concentration of the test samples used was not cytotoxic to the cells as determined by the gross morphological appearance of the monolayers. Also, no differences were observed in the cell viability tests using the MTT [3-(4,5-dimethylthiazol-2-yl) 2,5-diphenyltetrazolium bromide] assay in cultures incubated with and without the test samples. One set of flasks from each treatment was used for the MTT assay.

Observations

The results recorded are displayed below and presented in FIGS. 1 and 2.

TABLE 1

A Comparison of the Uptake of CoQ-10 from Cyclodextrin Complexes by Caco2 Cells

| | Cellular Total CoQ-10 (Treated/Control) Incubation Time (hrs) | | |
|---|---|---|---|
| Sample | 5 hr | 10 hr | 24 hr |
| CoQ-10 Powder | 1.0 | 1.0 | 1.0 |
| CoQ-10 Micelles | 1.981 | 2.074 | 4.124 |
| γ-Cyclodextrin Complex Freeze-dried | 18.771 | 27.567 | 34.0771 |
| γ-Cyclodextrin Complex Spray-dried | 9.650 | 16.162 | 24.219 |
| γ-Cyclodextrin Complex Vacuum-dried | 6.627 | 10.33 | 16.062 |
| β-Cyclodextrin Complex Freeze-dried | 10.887 | 13.783 | 17.038 |

FIG. 1 represents a comparison of uptake of CoQ-10 after 24-hours exposure. The cellular total CoQ-10 levels in the figures and table represent the ratio of sum of reduced and oxidized forms. The control represents the endogenous levels. A significant increase in the uptake of CoQ-10 was observed with the cyclodextrin complexes, as compared to the mixed micelles and the powder. The cellular CoQ-10 levels increased by nearly 34 times with the freeze-dried γ-cyclodextrin complex after 24 hours incubation. The uptake of CoQ-10 from the cyclodextrin complexes showed a distinct absorption curve, as can be seen in FIG. 2. The method of drying had a significant effect on the uptake of CoQ-10. The absorption followed the order freeze-dried>spray-dried>vacuum-dried. Complexation with p-cyclodextrin also significantly improved the uptake of CoQ-10 as compared to the powder and the micelles (FIGS. 1 and 2).

The results indicate that complexation with γ-cyclodextrin enhances the uptake of CoQ-10 from an aqueous dispersion even in the absence of micellarization. The uptake also is improved as compared to mixed micelles, the route for the intestinal absorption of lipophiles in vivo.

Example 2

In Vitro Uptake of CoQ-10 in Human Gingival Fibroblast Cells

Normal human gingival cells were used for the uptake studies. HGF-1 cells (ATCC, Rockville, Md.) were maintained in DMEM with 10% fetal bovine serum, glutamine, and pyruvate in a humidified atmosphere at 10% $CO_2$ and 37° C. The cells were allowed to reach confluency in 25 $cm^2$ flasks before the start of the experiment.

The stock test samples, prepared as in Example 1, were diluted in the culture medium for the experiment. CoQ-10 incorporated into liposomes was used for comparison. The CoQ-10-liposome stock solution was prepared using phosphatidylcholine and CoQ-10 in PBS. The components were dissolved in hexane and ethanol, mixed at specified concentrations (5% CoQ-10:95% phosphatidylcholine) and the solvent was evaporated using $N_2$. The residue was sonicated in PBS to obtain the liposomes.

The monolayers were washed with PBS before adding the test samples at known CoQ-10 concentration (100 μg/flask). The control flasks had an equivalent amount of PBS in the medium. The cultures were incubated as before and the CoQ-10 uptake was terminated at the end of 1 hr. The cells were processed, and the CoQ-10 extracted and estimated as detailed in Example 1.

Observations

The results recorded are displayed below and presented in FIG. 3.

TABLE 2

A Comparison of the Uptake of CoQ-10 from Cyclodextrin Complexes by Human Gingival Fibroblasts In Vitro

| Sample | Cellular Total CoQ-10 (Treated/Control) 1 hr Incubation |
|---|---|
| Liposomal CoQ-10 | 0.842 |
| γ-Cyclodextrin Complex Freeze-dried | 14.667 |
| γ-Cyclodextrin Complex Spray-dried | 11.756 |
| γ-Cyclodextrin Complex Vacuum-dried | 10.500 |
| β-Cyclodextrin Complex Freeze-dried | 9.756 |

The highest uptake was observed with the freeze-dried γ-cyclodextrin complex followed by the spray-dried and vacuum-dried complexes and the β-cyclodextrin complex. Complexation in general, significantly improved the uptake as compared to the liposomal preparation.

APPENDIX OF CITATIONS

Patent Documents

U.S.

1. Moldenhauser et al., U.S. Patent Application Publication No. 2003/0012774 A1
2. Hanioka et al., 6,461,593 (2002)

Foreign

1. JP59047202 (1984)
2. JP6089442(1985)
3. DE10139851 (WO203026603) (2003)
4. EP11174109(2002)
5. JP56109590 (1981)

Non-Patent Documents

1. Garrett, D. A., Failla, M. L., Sarama, R. J., and Craft, N., "Accumulation and retention of micellar β-carotene and lutein by Caco-2 human intestinal cells", *J. Nutr. Biochem.*, 10: 573–581, 1999.
2. Lutka, A. and Pawlaczyk, J., "Inclusion complexation of CoQ-10 with cyclodextrins", *Acta Pol. Pharm.*, 52:379–386, 1995.
3. Lutka, A. and Pawlaczyk, J., "Investigation of inclusion complexes of CoQ-10 with γ-cyclodextrin and methyl-β-cyclodextrin. Part I. Comparison of complexation methods in the solution state", *Acta Pol. Pharm.*, 53: 193–196, 1996a.
4. Lutka, A. and Pawlaczyk, J., "Investigation of inclusion complexes of CoQ-10 with γ-cyclodextrin and methyl-β-cyclodextrin. Part II. The influence of complexation temperature (heating method) on CoQ-10 solubility", *Acta Pol. Pharm.*, 53:197–201, 1996b.
5. Lutka, A. and Pawlaczyk, J., "Investigation of inclusion complexes of CoQ-10 with γ-cyclodextrin and methyl-β-cyclodextrin. Part III. The influence of cyclodextrins on CoQ-10 stability", *Acta Pol. Pharm.*, 54: 279–285, 1997.
6. Ono. N., Arima, H., Hirayama, F., and Uekema, K., "A moderate interaction of maltosyl-alpha-cyclodextrin with Caco2 cells in comparison with the parent cyclodextrin", *Biol. Pharm. Bull.*, 24: 395–402, 2001.
7. Puyol, P., Perez, M. D., Sanchez, L., Ena, J. M., and Calco, M., "Uptake and passage of beta lactoglobulin, palmitic acid and retinal across the Caco-2 monolayer", *Biochim. Biophys. Acta.*, 1236: 149–154,1995.
8. Shao, Z., Li, Y., Chermak, T., and Mitra, A. K, "Cyclodextrins as mucosal absorption promoters of insulin. II. Effects of beta-cyclodextrin derivatives on alpha-chymotryptic degradation and enteral absorption of insulin in rats", *Pharm Res.*, 11: 1174–9,1994.
9. Totterman, A. M., Schipper, N. G., Thompson, D. O., and Mannermaa, J. P., "Intestinal safety of water soluble beta-cyclodextrins in pediatric oral solutions of spironolactone: effects on human epithelial Caco-2 cells", *J. Pharm. Pharmacol.*, 49: 43–8,1997.
10. Traber, M. G., Goldberg, I., Davidson, E., Lagamy, N., and Kayden, H. J., "Vitamin E uptake by human intestinal cells during lipolysis in vitro", *Gastroenterology*, 98: 96–103,1990.
11. Turchanowa, M. V., Stein, L., and Caspary, W. F., "Transepithelial transport of putrescine across monolayers of the human intestinal epithelial cell line, Caco2", *World J. Gastroenterol.*, 7: 193–197, 2001.
12. Ueno, M., Ijitsu. T., Horiuchi, Y., Hirayama, F., Uekama, K., "Improvement of dissolution and absorption characteristics of ubidecarenone by dimethyl-β-cyclodextrin complexation", *Acta Pharm. Nord.*, 1: 99–104, 1989.

We claim:

1. A water-dispersible, freeze-dried bioavailable complex of coenzyme Q-10 and one or more of α-, β- or γ-cyclodextrin, wherein the molar ratio of cyclodextrin to coenzyme Q-10 rages from about 0.5:1 to 10:1.
2. The complex of claim 1, wherein said molar ratio ranges from about 1:1 to 2:1.
3. The complex of claim 1, wherein said cyclodextrin is one or more of β-cyclodextrin or γ-cyclodextrin.
4. The complex of claim 1, which formulated into one or more of a topical preparation, a sublingual formulation, or for oral ingestion.

5. A method for making a water-dispersible complex, which comprises the steps of:
   (a) preparing an aqueous slurry of a complex of coenzyme Q-10 and one or more of α-, β- or γ-cyclodextrin by adding coenzyme Q-10 to an aqueous dispersion of one or more of α-, β- or γ-cyclodextrin, wherein the molar ratio of cyclodextrin to coenzyme Q-10 rages from about 0.5:1 to 10:1; and
   (b) drying by one or more of spray drying, vacuum-drying, or freeze drying, said aqueous slurry to produce said complex.

6. The method of claim 5, wherein said molar ratio ranges from about 1:1 to 2:1.

7. The method of claim 5, wherein said cyclodextrin is one or more of β-cyclodextrin or γ-cyclodextrin.

8. In a method for administering to an animal in need thereof a bioavailable
   (a) preparing a water-dispersible complex of coenzyme Q-10 and one or more of α-, β- or γ-cyclodextrin by adding coenzyme Q-10 to an aqueous dispersion of one or more of α-, β- or γ-cyclodextrin, wherein the molar ratio of cyclodextrin to coenzyme Q-10 rages from about 0.5:1 to 10:1; and
   (b) administering said complex to said animal.

9. The method of claim 8, wherein said animal is a human.

10. The method of claim 8, wherein said complex is ingested by said animal.

11. The method of claim 8, wherein said molar ratio ranges from about 1:1 to 2:1.

12. The method of claim 8, wherein said cyclodextrin is one or more of β-cyclodextrin or γ-cyclodextrin.

13. The method of claim 8, wherein said complex is prepared by freeze-drying.

14. The method of claim 8, which formulated into one or more of a topical preparation, a sublingual formulation, or for oral ingestion.

15. The method of claim 8, wherein said cyclodextrin is one or more of β-cyclodextrin or γ-cyclodextrin.

16. A method for making a water-dispersible complex, which comprises the steps of:
   (a) preparing an aqueous slurry of a complex of coenzyme Q-10 and one or more of α-, β- or γ-cyclodextrin by adding coenzyme Q-10 to an aqueous dispersion of one or more of α-, β- or γ-cyclodextrin at room temperature using homogenization followed by storage under refrigeration; and
   (b) drying by one or more of spray drying, vacuum-drying, or freeze drying, said aqueous slurry to produce said complex.

17. In a method for administering to an animal in need thereof a bioavailable coenzyme Q-10 complex, said coenzyme Q-10 being useful for treating disease conditions comprising cardiovascular disease, periodontal disease, high blood pressure, Parkinson's disease, skin care, and oral health care, which comprises the steps of:
   (a) preparing a water-dispersible complex of coenzyme Q-10 and one or more of α-, β- or γ-cyclodextrin by adding coenzyme Q-10 to an aqueous dispersion of one or more of α-, β- or γ-cyclodextrin at room temperature using homogenization followed by storage under refrigeration; and
   (b) administering said complex to said animal.

* * * * *